(12) United States Patent
Bengtsson et al.

(10) Patent No.: US 10,335,535 B2
(45) Date of Patent: Jul. 2, 2019

(54) INJECTION DEVICE WITH A NEEDLE CANNULA

(71) Applicant: Novo Nordisk A/S, Bagsvaerd (DK)

(72) Inventors: Henrik Bengtsson, Taastrup (DK);
Lars Eilertsen, Fredensborg (DK);
Casper Bo Jensen, Lyngby (DK);
Frederik Kaae Kirk, Copenhagen NV (DK)

(73) Assignee: Novo Nordisk A/S, Bagsvaerd (DK)

( * ) Notice: Subject to any disclaimer, the term of this patent is extended or adjusted under 35 U.S.C. 154(b) by 174 days.

(21) Appl. No.: 15/032,482

(22) PCT Filed: Oct. 10, 2014

(86) PCT No.: PCT/EP2014/071746
§ 371 (c)(1),
(2) Date: Apr. 27, 2016

(87) PCT Pub. No.: WO2015/062845
PCT Pub. Date: May 7, 2015

(65) Prior Publication Data
US 2016/0271319 A1  Sep. 22, 2016

Related U.S. Application Data

(60) Provisional application No. 61/899,413, filed on Nov. 4, 2013.

(30) Foreign Application Priority Data

Oct. 31, 2013  (EP) ..................................... 13191052

(51) Int. Cl.
*A61M 5/00* (2006.01)
*A61M 5/32* (2006.01)
(Continued)

(52) U.S. Cl.
CPC .............. *A61M 5/001* (2013.01); *A61M 5/24* (2013.01); *A61M 5/2466* (2013.01);
(Continued)

(58) Field of Classification Search
CPC .............. A61M 5/2448; A61M 5/2466; A61M 5/3204; A61M 5/3213; A61M 2005/3267;
(Continued)

(56) References Cited

U.S. PATENT DOCUMENTS 3,354,881 A   11/1967  Bloch
4,392,859 A   7/1983   Dent
(Continued)

FOREIGN PATENT DOCUMENTS

EP   0252644 A2   1/1988
JP   S6324955 A   2/1988
(Continued)

*Primary Examiner* — Nathan R Price
*Assistant Examiner* — Justin L Zamory
(74) *Attorney, Agent, or Firm* — Wesley Nicolas

(57) ABSTRACT

The present invention relates to an injection device for injecting a pharmaceutical liquid drug containing a preservative. The injection device comprises a housing (1) supporting a cartridge (20) having an interior chamber (21) holding the pharmaceutical preservative containing liquid drug to be injected, and a needle cannula (10) having a front part (11) and a back part (12), which back part (12) is adapted to be in liquid communication with the interior chamber (21) of the cartridge (20). The injection device is further provided with a telescopic needle covering shield (30) which distally is provided with a reservoir (31) which holds a liquid containing the same preservatives as in the pharmaceutical preservative containing liquid drug contained in the interior chamber of the cartridge. The telescopic needle covering shield (30) is telescopic movable in relation to the needle cannula (10) by a first resilient member (Continued)

between a first position and a second position. In the first position, the tip (13) of the front part (11) of the needle cannula (10) is maintained inside the reservoir (31), and in the second position, the tip (13) of the front part (11) of the needle cannula (10) is located outside the reservoir (31) and distally to the reservoir (31). The tip (13) of the needle cannula (10) is thus cleaned by the preservatives in the reservoir (31) between subsequent injections.

7 Claims, 5 Drawing Sheets

(51) Int. Cl.
    *A61M 5/24*     (2006.01)
    *A61M 5/31*     (2006.01)

(52) U.S. Cl.
    CPC .......... *A61M 5/3204* (2013.01); *A61M 5/326* (2013.01); *A61M 5/3213* (2013.01); *A61M 2005/2474* (2013.01); *A61M 2005/3115* (2013.01); *A61M 2005/3121* (2013.01); *A61M 2005/3267* (2013.01)

(58) Field of Classification Search
    CPC .. A61M 2005/2474; A61M 2005/3115; A61M 2005/3121
    See application file for complete search history.

(56) References Cited

U.S. PATENT DOCUMENTS

| | | | |
|---|---|---|---|
| 4,416,663 A * | 11/1983 | Hall | A61M 5/326 604/198 |
| 4,666,436 A | 5/1987 | McDonald et al. | |
| 4,775,376 A | 10/1988 | Strung | |
| 5,292,314 A | 3/1994 | D'Alessio et al. | |
| 5,894,015 A | 4/1999 | Rechtin | |
| 9,107,419 B2 | 8/2015 | Fallon et al. | |
| 2005/0142180 A1 * | 6/2005 | Bisgaier | A61K 9/0019 424/450 |
| 2013/0090604 A1 * | 4/2013 | Davies | A61M 5/2448 604/191 |

FOREIGN PATENT DOCUMENTS

| | | |
|---|---|---|
| JP | H03178671 A | 8/1991 |
| JP | 2012514602 A | 6/2012 |
| WO | 9611026 A1 | 4/1996 |
| WO | 2008/077706 A1 | 7/2008 |

\* cited by examiner (First position)

(Second position)

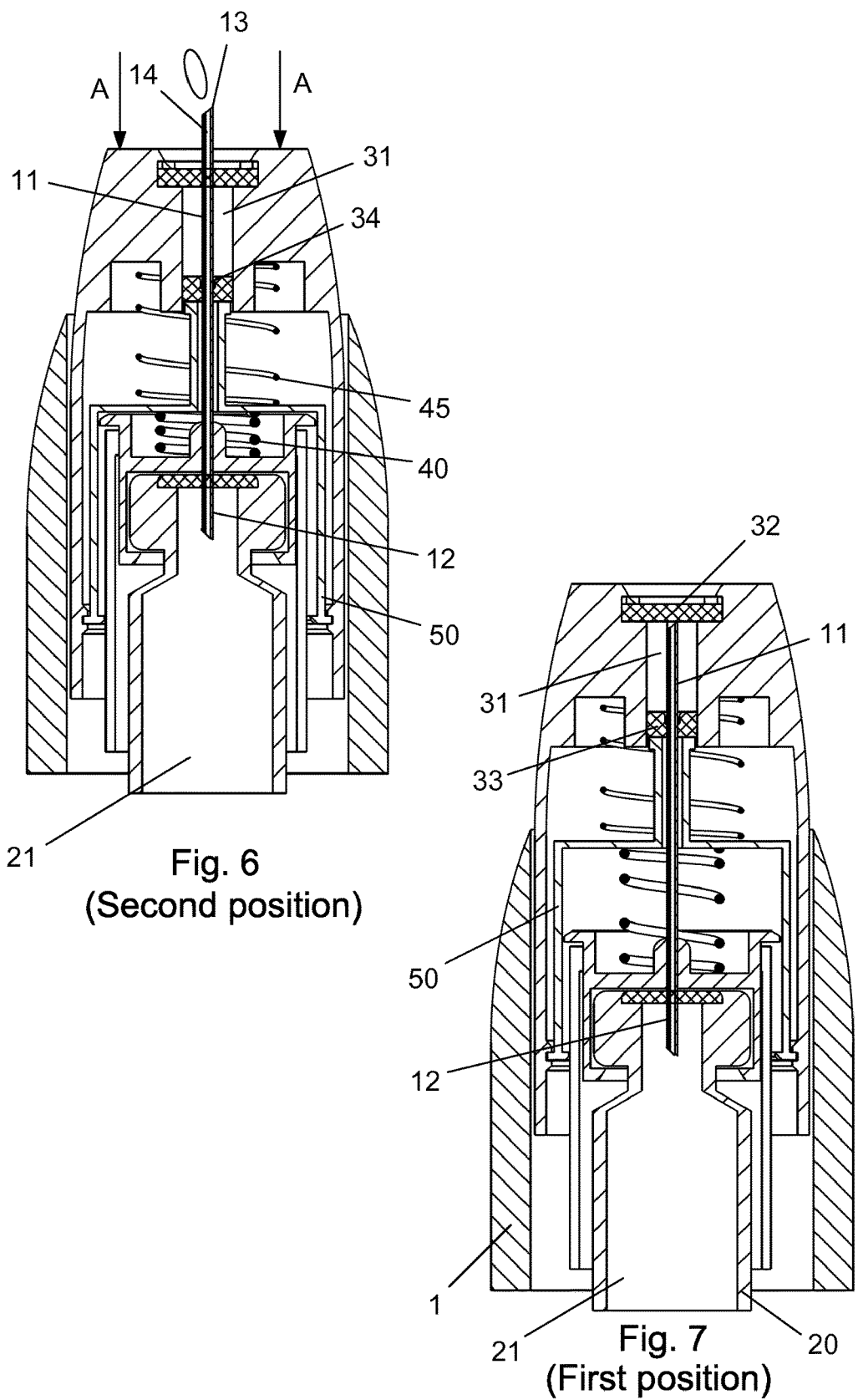
Fig. 6 (Second position)
Fig. 7 (First position)

INJECTION DEVICE WITH A NEEDLE CANNULA

CROSS-REFERENCE TO RELATED APPLICATIONS

This application is a 35 U.S.C. § 371 National Stage application of International Application PCT/EP2014/071746 (published as WO 2015/062845), filed Oct. 10, 2014, which claims priority to European Patent Application 13191052.3, filed Oct. 31, 2013; this application claims priority under 35 U.S.C. § 119 to U.S. Provisional Application 61/899,413, filed Nov. 4, 2013.

THE TECHNICAL FIELD OF THE INVENTION

The invention relates to an injection device such as an injection pen preferably in combination with a needle cannula. The invention especially relates to such injection device wherein the same needle cannula is used for multiple successive injections and automatically cleaned between injections. Further, the invention relates to a method of preparing such injection device.

DESCRIPTION OF RELATED ART

Shielded injection needle assemblies are known from e.g. WO 2008/077706 and U.S. Pat. No. 5,292,314. Further, a syringe having a manually operational telescopic shield is disclosed in EP 252,644 (FIG. 11-13). When the user needs to purge this syringe, a variable quantum of the drug contained in the syringe is ejected into a purging chamber forming the telescopic shield. Prior to purging the syringe, the user must manually manipulate the telescopic shield into the correct position. When purging the syringe, the user determines the volume ejected into the chamber of the shield.

Injection devices having an injection needle for repetitive use is disclosed in U.S. Pat. Nos. 3,354,881 and 4,416,663. These injection devices for repetitive use have a telescopic movable shield which covers the tip of needle cannula between injections. The telescopic shield is pushed to its initial covering position by resilient means, which in U.S. Pat. No. 4,416,663 is identified as being a spring. Further, the telescopic shield is provided with a reservoir containing a cleaning agent for cleaning the tip of the needle cannula between injections. The cleaning agent is in both U.S. Pat. Nos. 3,354,881 and 4,416,663 referred to as a sterilizing fluid.

However, as the injection needle is maintained attached to the injection device between injections, the sterilizing fluid can flow through the lumen of the needle cannula and into the interior of the cartridge and thus be mixed with the pharmaceutical liquid drug contained in the cartridge and thus contaminate the drug. The result being that next time an injection is performed, the sterilizing fluid that has flown into the cartridge is injected into the body of the user together with the pharmaceutical liquid drug of the cartridge.

DESCRIPTION OF THE INVENTION

It is an object of the present invention to provide an injection device with a needle cannula for repetitive use and wherein the liquid pharmaceutical drug contained in the cartridge is not contaminated by the cleaning liquid contained in the reservoir of the telescopic shield and which operates without the use of cumbersome physical valves or the like.

The invention is defined in the claims. Accordingly, in a first aspect the present invention relates to an injection device comprising the following details:
- a housing holding a cartridge having an interior chamber containing the pharmaceutical liquid drug to be injected. The pharmaceutical liquid drug contains a preservative maintaining the liquid drug biostatic i.e. prevents the growth or multiplication of an organism especially a microorganism in the liquid drug.
- a needle cannula usable for multiple injections having a front part and a back part. The back part is adapted to be in liquid communication with the interior chamber of the cartridge and the front part has a sharp tip adapted to penetrate the skin of a user, and
- a telescopic needle covering shield which distally is provided with a reservoir holding a predetermined volume of a liquid for cleaning at least the tip of the needle cannula between subsequent injections. The telescopic needle shield is urged in a distal direction by a resilient member, preferably a compression spring operational located between the telescopic needle shield and the housing The telescopic movable needle covering shield is axially and telescopic movable in relation to the needle cannula between a first position and a second position. The first and the second position being defined as;
- a first position in which the tip of the front part of the needle cannula is maintained inside the reservoir, and
- a second position in which the tip of the front part of the needle cannula (10) is located outside the reservoir and distally to the reservoir.

In order to prevent contamination of the pharmaceutical liquid drug contained inside the cartridge, the liquid in the cleaning reservoir of the shield contains the same preservatives as present in the pharmaceutical preservative containing liquid drug inside the cartridge. In this way a backflow of liquid through the lumen of the needle cannula from the reservoir of the telescopic shield and back into the chamber of the cartridge will not contaminate the liquid drug inside the cartridge as the same preservatives are present in both liquids. The backflow will thus only very marginally raise the concentration of preservatives inside the chamber of the cartridge.

The volume of liquid in the reservoir of the telescopic shield is predetermined by the manufacture of the injection device and is preferably predetermined such that the tip of the needle cannula is fully submerged in the liquid between subsequent injections. This implies that the level to which the reservoir of the shield is filled must be sufficient to maintain at least the tip of the needle cannula submerged in the liquid in all situations.

The injection device can be any kind of pre-filled or durable injection device. The drive mechanism of the injection device can be either manual or spring-loaded. By manual is meant that the user delivers the force needed to press the liquid drug out of the cartridge and by spring-loaded is meant that a spring, compression or torque, is provided in the injection and utilized, fully or partly, to press the liquid drug out through the lumen of the attached needle cannula.

The liquid in the reservoir of the telescopic shield is in a preferred example either phenol or metacresol or any combination thereof. The preservatives can also be provided inside the reservoir of the telescopic shield in a solution of sterile injectable water. However, most beneficial is to use the pharmaceutical preservative containing liquid drug in the injection device as the cleaning liquid in the reservoir. The pharmaceutical preservative containing liquid drug inside the cartridge and inside the reservoir of the telescopic shield is thus the identical same. In a preferred example, the liquid drug is a blood sugar regulating drug such as insulin, insulin analogue, GLP-1 or GLP-2. In a further example the pharmaceutical preservative containing liquid drug could be a growth hormone. The pharmaceutical preservative containing liquid drug could in an example be any commercially available liquid drug from the company Novo Nordisk A/S, e.g., NovoRapid®, NovoLog®, Levemir®, NovoMix®, Tresiba®, Ryzodeg®, Xultophy®, Victoza®, Saxenda® or Norditropin®, which all contains a preservative maintaining the liquid drug biostatic.

The needle cannula is in one example permanently secured to the injection device. Alternatively the needle cannula can be secured in a hub by gluing, welding or the like. The hub is then either permanently secured to the injection device, or provided with connecting means for detachable connecting the hub to the injection device. In the example wherein the hub is detachable coupled to the injection device, the telescopic shield could be provided in conjunction with the hub to form a part of the needle assembly. When the needle cannula is permanently secured to the injection device, either directly or via a hub, the preferred device is a so-called pre-filled injection device.

In one example, the reservoir of the telescopic shield is made as a through-going opening in the telescopic shield which distally is covered by a distal membrane and proximally covered by a proximal membrane. These membranes or septums are preferably made from a rubber composition as known from standard septums generally used in cartridges.

In an example one of these membranes or septums and preferably the proximal septum of the reservoir could be movable in relation to the telescopic shield. This movement of the proximal septum is preferably in a proximal direction thus allowing the reservoir to be filled.

In the initial position when the proximal surface of the distal septum abuts the distal surface of the proximal septum a carved-out portion in one or both of the septums is preferred such that the lumen of the needle cannula is not covered by the septum material in the initial position. When such carved-out portion is present, a reservoir is so to speak formed even in the abut situation such that the liquid pharmaceutical drug has a space to flow into when an initial quantum is ejected into the reservoir.

The filling of the reservoir is preferably done fully automatically and preferably by automatically moving the proximal septum in a proximal direction such that a vacuum is created inside the so expanding reservoir of the telescopic shield. In this context automatically means that the injection device is provided with means which generates the movement of the proximal septum. The means generating this proximal movement is preferably resilient means such as spring or like element. The proximal septum can in one particular embodiment be moved axially in the proximal direction by a pull spring which is e.g. released upon first use of the injection device.

The axial movement of the proximal septum and thus the vacuum created and the filling volume of the reservoir in the telescopic shield is determined by the manufacture of the injection device. It can be inherent in the force of the spring or various stops can be provided limiting the distance the proximal septum can move. In any way, the volume of liquid filled into the reservoir is solely determined by the manufacture of the injection device such that the injection device is delivered to the user with this predetermination being inherent in the injection device. The user thus only has to take the injection device into use following the instructions from the manufacturer where after, the reservoir will be automatically filled with the predetermined volume.

In one example, the proximal septum is preferably secured to an axial movable element which moves axially under influence of the second spring. The movable element preferably moves proximally from a locked position to a position engaging the telescopic shield when a user operates a release mechanism which again can be automatically released first time a user sets a dose.

Alternatively, the injection device automatically ejects a predetermined volume of the pharmaceutical preservative containing liquid drug into the reservoir upon first use of the injection device. In one embodiment, the cap of the injection device can be coupled to a mechanism which automatically slides the cartridge proximally such that the rubber piston inside the cartridge is relatively moved to press out a predetermined volume. This ejection mechanism could e.g. be coupled to the cap such that it is activated upon rotation of the cap.

The invention further includes a method of preparing the injection device prior to performing a series of injections i.e. the method is preferably executed when a new injection device is taken into use. The injection device is preferably a pre-filled injection device which is only taken into use once and discarded when the cartridge is empty after a series of injections.

In order to take the pre-filled injection device into use, the user needs to perform two simple operations. The method according to the invention therefore comprises of at least the following two steps:
  i) holding the injection device with the telescopic shield in the first position such that the tip of the needle cannula is located inside the reservoir of the telescopic shield, and
  ii) automatically transferring a predetermined volume of the pharmaceutical preservative containing liquid drug contained inside the chamber of the cartridge into the reservoir of the telescopic shield.

According to this method the user must first secure that the tip of the needle cannula is inside the reservoir of the telescopic shield where after the release mechanism must be activated such that the predetermined volume is automatically transferred from the compartment of the cartridge and into the reservoir of the telescopic shield.

The release mechanism can be a movable element that the user must physically remove in order to activate the release or it can be integrated with the dose setting mechanism such that it is released first time the user sets a dose to be injected.

The volume automatically filled into the reservoir is determined by the manufacture of the injection device. It can be decided by the size of the vacuum generated which again can be a result of the spring force of the spring used to generate the vacuum. Alternatively it can be one or more physical stops provided in the injection device; stops which e.g. limits the axial movement of the proximal septum.

This method is in a further embodiment performed by releasing the movable element such that the second spring drives the movable element and the proximal septum in the proximal direction thereby creating a vacuum inside the reservoir. As the proximal septum moves further in the proximal direction, this vacuum grows and the pharmaceutical preservative containing liquid drug is automatically sucked through the lumen on the needle cannula from the chamber of cartridge and into the reservoir of the telescopic shield.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and connected to a hub to form a complete injection needle also often referred to as a "needle assembly". A needle cannula could however also be made from a polymeric material or a glass material. The hub also carries the connecting means for connecting the needle assembly to an injection apparatus and is usually moulded from a suitable thermoplastic material. The "connection means" could as examples be a luer coupling, a bayonet coupling, a threaded connection or any combination thereof e.g. a combination as described in EP 1,536,854.

The term "Needle unit" is used to describe one single needle assembly carried in a container. Such container usually has a closed distal end and an open proximal end which is sealed by a removable seal. The interior of such container is usually sterile such that the needle assembly is ready-to-use. Needle units specially designed for pen injections systems are defined in ISO standard No. 11608, part 2, and are often referred to as "pen needles". Pen needles have a front part for penetrating into the user and a back part for penetrating into the cartridge containing the drug.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form. Further, the term "Preservative containing liquid drug" is meant to encompass any flowable drug containing any amount of a preservative. In one example the preservative could be a phenol or a metacresol or any combination thereof. However, the wording preservative containing should not be limited to only these substances but should indeed mean any combination of a flowable drug and a preservative.

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

The term "Permanently secured" as used in the description is intended to mean that the parts, which in this application is embodied as the needle cannula and the injection device, requires the use of tools in order to be separated and should the parts be separated it would permanently damage at least one of the parts.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 6 show a cross sectional view of part of the injection device of a second embodiment during dose expelling.

FIG. 7 show a cross sectional view of part of the injection device of a second embodiment between successive injections.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENTS

When in the following terms as "upper" and "lower", "right" and "left", "horizontal" and "verti-cal", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the tip 13 of the needle cannula 10 actually penetrating the skin of the user whereas the term "proximal end" is meant to refer to the opposite end pointing away from the user during injection and penetrating into the cartridge 20.

Figure 1:
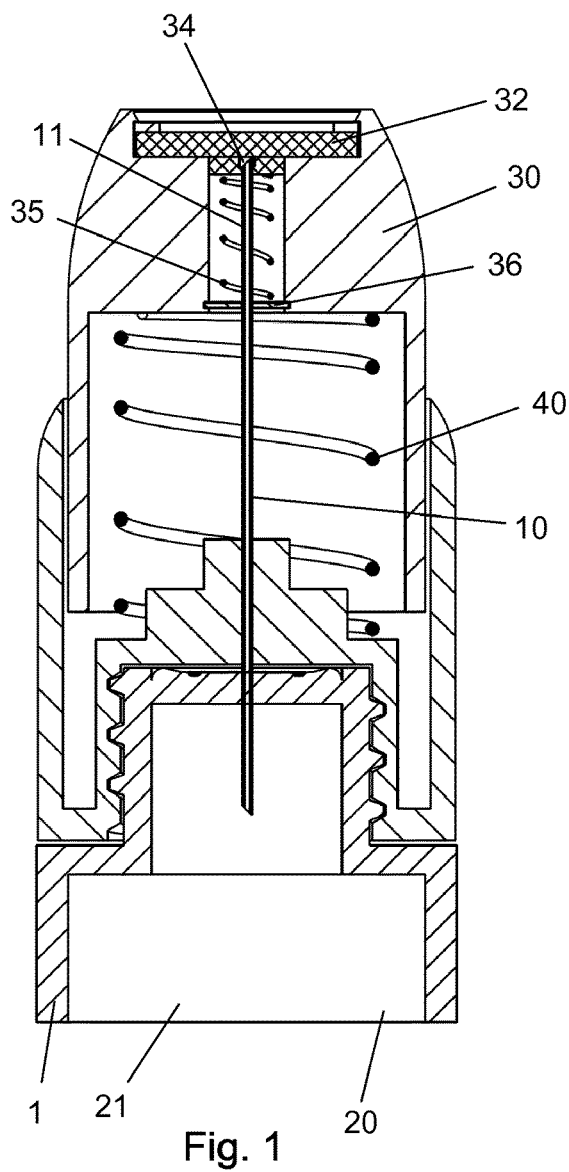
FIG. 1 show a cross sectional view of part of the injection device prior to use.
Figure 2:
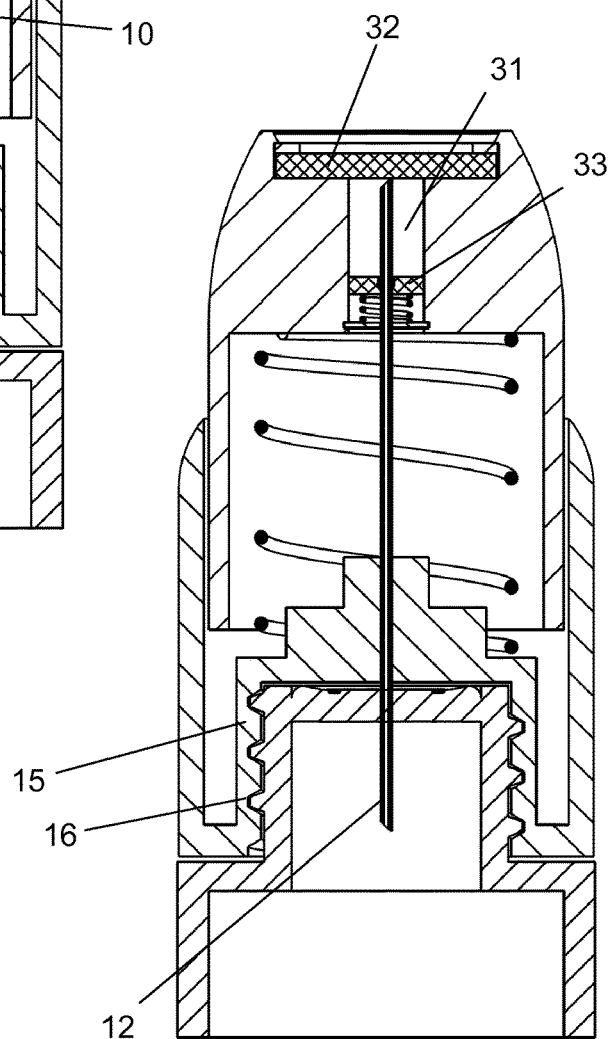
FIG. 2 show a cross sectional view of part of the injection device during filling of the reservoir of the telescopic shield.
Figure 3:
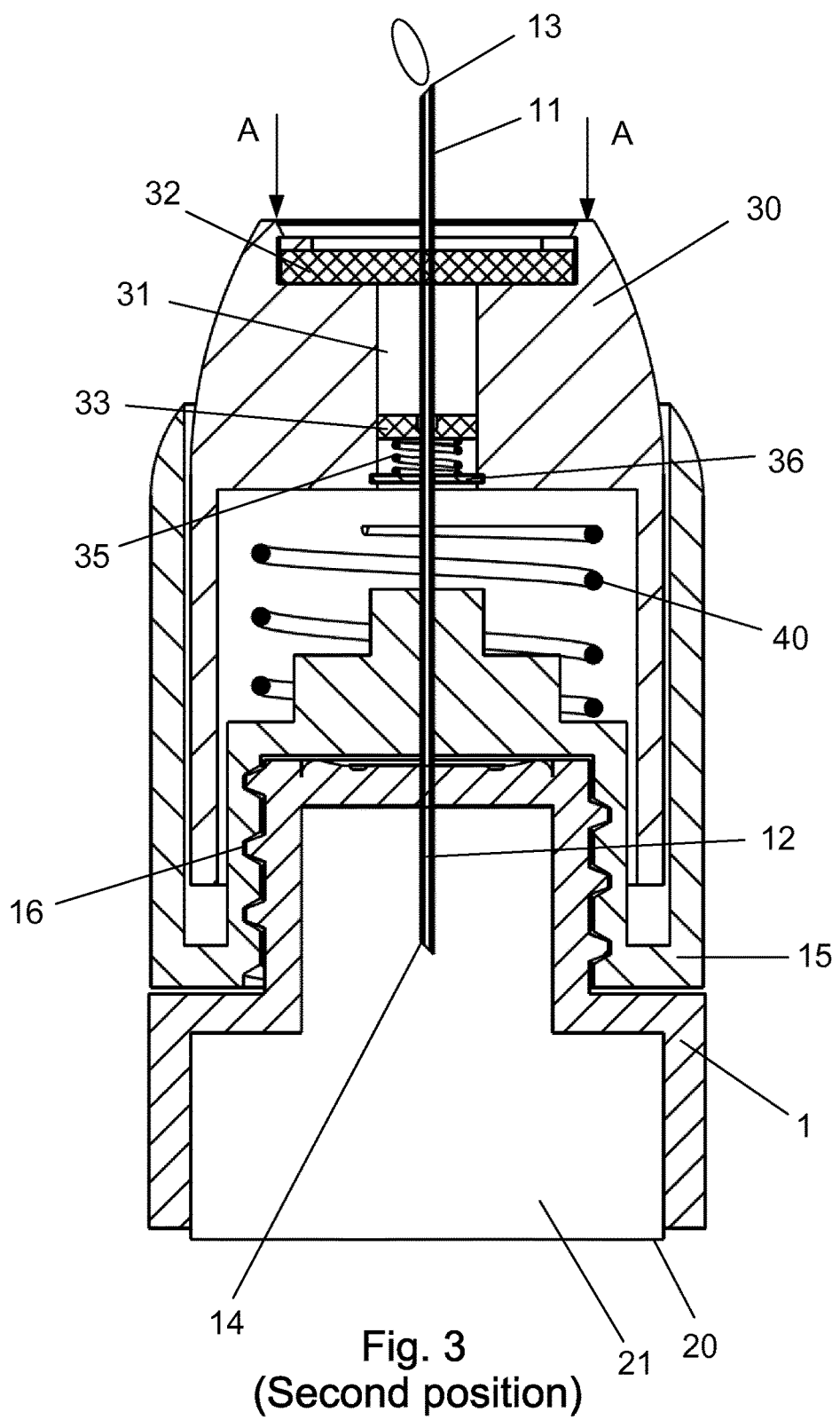
FIG. 3 show a cross sectional view of part of the injection device during dose ejection.

FIGS. 1 to 3 discloses the first embodiment in which an injection device carries a needle cannula 10. The needle cannula 10 is in the depicted embodiment secured in a hub 15 which is removable connected to a housing 1 of the injection device by a thread 16. However, the needle cannula 10 could be secured to the housing 1 in many different ways. The needle cannula 10 could e.g. be formed permanently attached to the housing 1.

The needle cannula 10 has a front part 11 provided with a grinded tip 13 for easy piercing of the skin of a user and a back part 12 for penetrating into a chamber 21 of a cartridge 20. The opposite cannula end could also be grinded, and the two ends are connected through a lumen 14.

Distally the housing 1 is provided with a telescopic shield 30 which is urged in the distal direction by a first resilient element such as a first spring 40 such that the telescopic shield 30 conceals the tip 13 of the needle cannula 10 in a non-use situation i.e. when not injecting.

The telescopic shield 30 is further provided with a reservoir 31 which in the disclosed embodiment is depicted as a cylindrical through-going opening which distally is sealed by a distal septum 32 and proximally is sealed by a proximal septum 33 such that the through-going opening forms the reservoir 31.

Either the distal septum 32 or the proximal septum 33, or both septums 32, 33, can on the surface pointing towards the reservoir 31 be provided with a carved-out portion 34 which in the first position could make up the reservoir 31 as depicted in FIG. 1.

Further, a pull spring 35 is encompassed between, and connected to, the proximal septum 33 and a wall 36 which again is secured to the telescopic shield 30. The wall 36 could also be moulded as an integral part of the telescopic shield 30. This wall 36 together with the proximal septum 33 also supports and guides the needle cannula 10 thus preventing the front part 11 of the needle cannula 10 from bending when passing through the distal septum 32.

In FIG. 1, the injection device is depicted with the telescopic shield 30 positioned in the first position. The telescopic shield 30 is urged in the distal direction by the spring 40 and the tip 13 of the needle cannula 10 is located inside the reservoir 31 (represented by the carved-out portion 34).

The pull spring 35 is in FIG. 1 depicted in its cocked position where it is held stretched out by a not-shown release mechanism. When this release mechanism is released, preferably by the user, the pull spring 36 pulls the proximal septum 33 in a proximal direction as disclosed in FIG. 2. This movement creates a vacuum inside the reservoir 31, which vacuum moves a part of the pharmaceutical preservative containing liquid drug from the chamber 21 of the cartridge 20 to the reservoir 31 via the lumen 14 of the needle cannula 10.

Alternatively, the proximal septum 33 could be in a permanent position thus defining the reservoir 31 with a fixed volume. In this case, the drive mechanism of the injection device could be set to inject a predetermined amount of pharmaceutical preservative containing liquid drug into the reservoir 31 the first time the injection device is taken into use. It would then be preferred if one of the septums 32, 33 were provided with a venting area through which the air trapped in the reservoir 31 could escape during filling of the reservoir 31.

The tip 13 of the needle cannula 10 is in FIG. 2 submerged into a quantum of the pharmaceutical liquid drug and since a pharmaceutical liquid drug usually contains preservative substances, these preservatives will clean the tip 13 of the needle cannula 10 whenever the tip 13 is inside the reservoir 31.

When a user presses the injection device against the skin as indicated by arrows "A" in FIG. 3, the telescopic shield 30 is pushed in the proximal direction into its second position against the bias of the first spring 40. The front part 11 of the needle cannula 10 and especially the tip 13 of the needle cannula 10 thus penetrates through the distal septum 32 and an injection can be performed either manually or automatically.

Following the injection when the user removes the telescopic shield 30 from the skin, the telescopic shield 30 is urged into the first position by the first spring 40 which makes the tip 13 of the needle cannula 10 once again enter into its submerged position inside the reservoir 31 as depicted in FIG. 2.

In a second embodiment disclosed in the FIGS. 4 to 7, the same elements are numbered using the same numbers as in the first embodiment.

Figures 4, 5:
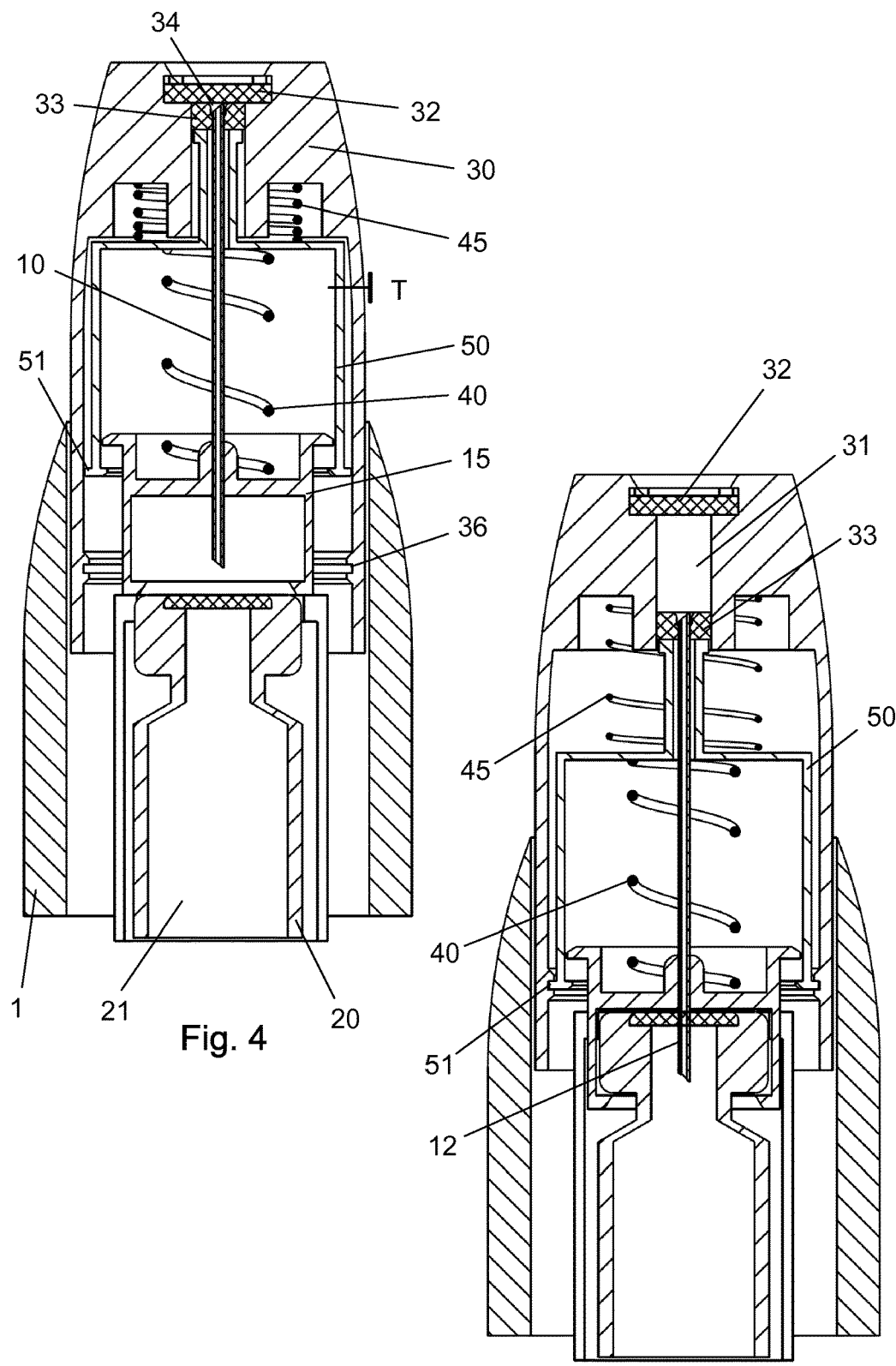
FIG. 4 show a cross sectional view of part of the injection device of a second embodiment prior to use.
FIG. 5 show a cross sectional view of part of the injection device of a second embodiment during filling of the reservoir of the telescopic shield.

FIG. 4 discloses the injection device with the telescopic shield 30 in the first position. The needle cannula 10 is mounted in a telescopic movable hub 15 and the telescopic shield 30 is urged in a distal direction by the first spring 40. The tip 13 of the needle cannula 10 is located inside the reservoir 31 which in FIG. 4 is limited to the carved-out portion 34. In the depictured embodiment this carved-out portion 34 is formed in the proximal septum 33 but it could easily be provided in the distal septum 32 or in both septums 32, 33.

The proximal septum 33 is carried by a movable element 50 which is urged in the proximal direction by a second spring 45. A not disclosed release mechanism secures the movable element 50 and prevents it from moving proximally before the user actually activates the injection device. This release mechanism could in a simple form e.g. be a tab (indicated as "T" in FIG. 4) that the user must remove before first use of the injection device. A similar tab could be provided in the first embodiment to secure the pull spring 35 in its stretched condition. The release mechanism could alternatively be coupled to the dose dial, such that once a dose is being dialled, the movable element 50 is released and moves automatically in the proximal direction under the influence of the second spring 45. This proximal movement presses the hub 15 over the distal end of the cartridge 20 such that the back part 12 of the needle cannula 10 enters into liquid communication with the chamber 21 of the cartridge 20.

The coupling between the hub 15 and the cartridge 20 is in the depicted embodiment designed such that the back part 12 of the needle cannula 10 thereafter remains in this liquid communicating position as will be explained.

As the movable element 50 slides in the proximal direction so does the proximal septum 33 thus creating a vacuum inside the reservoir 31. This vacuum draws a predetermined quantum of the pharmaceutical liquid drug from the chamber 21 of the cartridge 20 and through the lumen 14 of the needle cannula 10 into the reservoir 31 which in this way is automatically filled.

FIG. 5 discloses the movable element 50 in its proximal position in which a radial ridge 51 provided on the movable element 50 is locked in a similar groove 36 provided internally in the telescopic shield 30 such that the movable element 50 thereafter moves telescopic together with the telescopic shield 30.

When a user performs an injection by pressing the distal end of the telescopic shield 30 against the skin as indicated by the arrows "A" in FIG. 6, both the telescopic shield 30 and the movable element 50 retracts together thus maintaining the reservoir 31 with the same constant volume.

Once the injection has been given, either manually by pressing home an extended element or automatically by an electric- or spring motor, the user removes the telescopic shield 30 from his or hers skin where after the first spring 40 urges the telescopic shield 30 and the movable element 50 distally such that the tip 13 of the needle cannula 10 re-enters into the reservoir 31 where it is maintained submerged in the cleaning liquid until the next injection.

When the telescopic shield 30 moves axially from the second position disclosed in FIG. 6 to the first position disclosed in FIG. 5, the tip 13 of the needle cannula 10 once again enters into the reservoir 31 to be cleaned and be kept clean until next injection.

Figure 8:
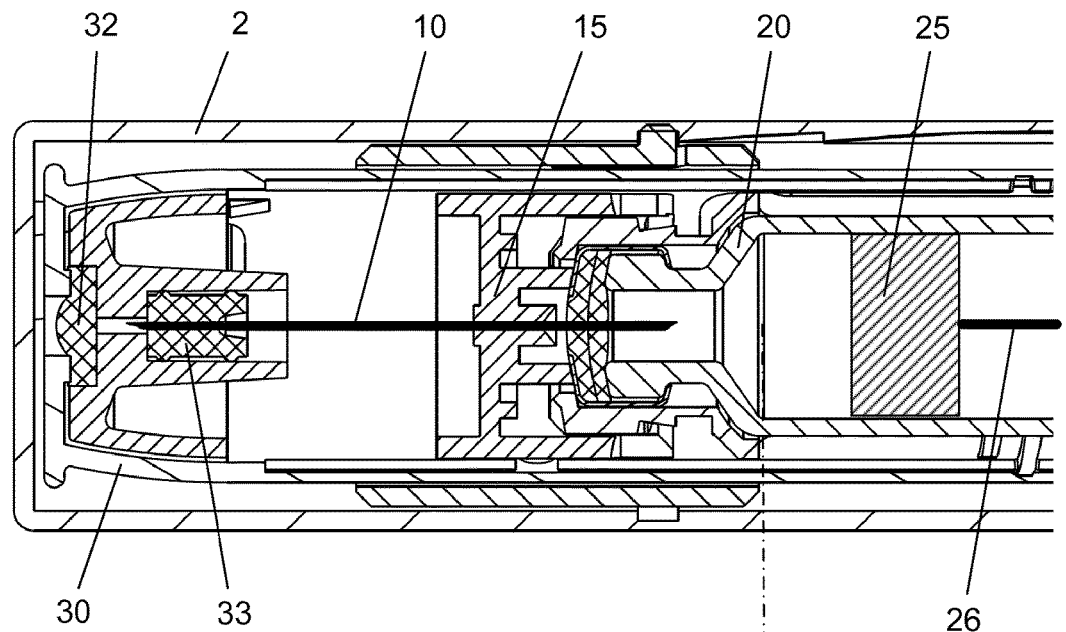
FIG. 8 show a cross sectional view of another embodiment prior to use.
Figure 9:
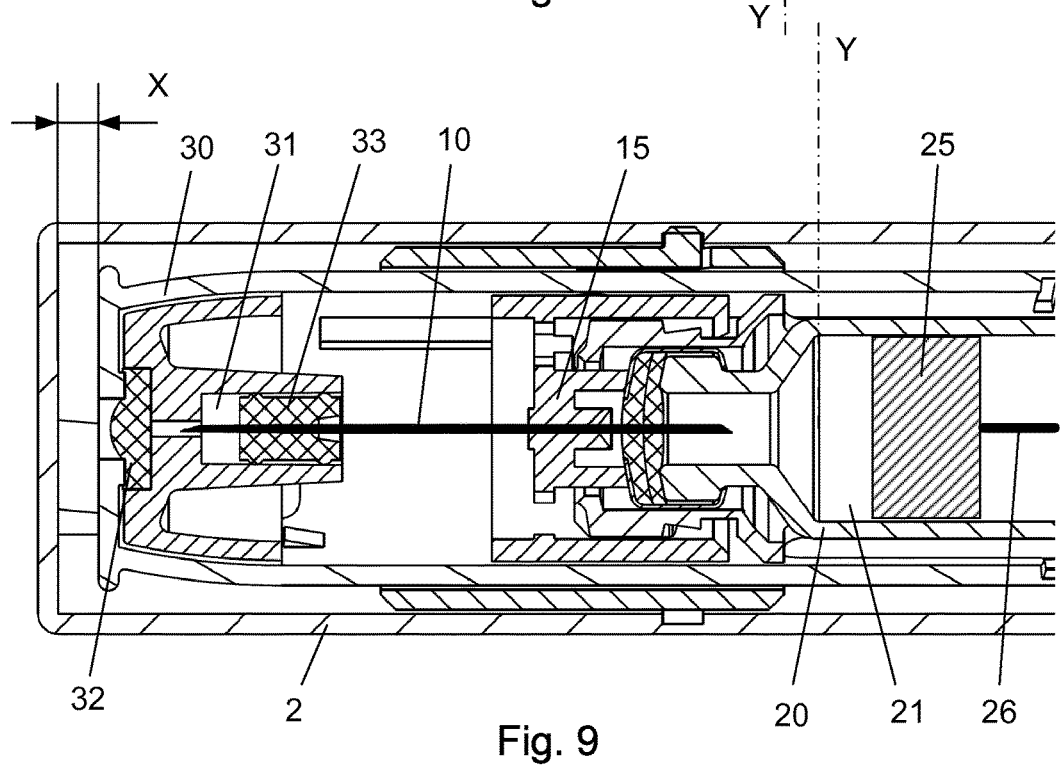
FIG. 9 show the embodiment of FIG. 8 during filling of the reservoir of the telescopic shield.

Yet another embodiment is disclosed in FIG. 8-9 in which the same numbering of the various elements have been maintained.

The pharmaceutical liquid preservative containing drug is pressed out through the lumen 14 of the needle cannula 10 by moving a rubber piston 25 forward inside the cartridge 20 thereby decreasing the volume of the chamber 21. In order to move the rubber piston 25 forward a piston rod 26 is driven in the distal direction by a not-shown drive mechanism.

In FIG. 8, the distal end of the injection device is located inside a protective cap 2 as is common with injection devices. This cap 2 is coupled to the injection device such that when a user rotates the cap 2, the distal part of the injection device is forced to move proximally. However, the rubber piston 25 remains in its previous position due to the piston rod 26 which is locked against any proximal movement by the drive mechanism.

As the cap 2 is rotated the injection device moves the distance "X" in the proximal direction as depicted in FIG. 9.

This movement also moves the cartridge axially a distance "Y" in relation to the rubber piston 25 thereby ejecting a predetermined amount of the pharmaceutical liquid preservative containing drug into the reservoir 31.

Example of a pharmaceutical preservative containing liquid drug:

In one specific example, the liquid pharmaceutical drug contained in the chamber 21 of the cartridge 20 and in the reservoir 31 of the telescopic shield 30 could be NovoLog®, which is manufactured and sold by Novo Nordisk A/S.

NovoLog® is a sterile, aqueous, clear, and colourless solution that contains:
insulin aspart 100 Units/mL
glycerin 16 mg/mL
phenol 1.50 mg/mL
metacresol 1.72 mg/mL
zinc 19.6 mcg/mL
disodium hydrogen phosphate dehydrate 1.25 mg/mL
sodium chloride 0.58 mg/mL
water for injection NovoLog has a pH of 7.2-7.6 and Hydrochloric acid 10% and/or sodium hydroxide 10% may be added to adjust pH.

The preservatives (phenol and metacresol) are simultaneously present both in the chamber 21 of the cartridge 20 and in the reservoir 31 of the telescopic shield 30. Since the liquid in the chamber 21 and in the reservoir 31 is the same pharmaceutical preservative containing liquid drug, the exchange of liquid through the lumen 14 of the needle cannula 10 has no influence on the pharmaceutical preservative containing liquid drug to be injected as only the identical same pharmaceutical preservative containing liquid drug is present in the chamber 21 of the cartridge 20 and in the reservoir 31 of the telescopic shield 30.

Some preferred embodiments have been shown in the foregoing, but it should be stressed that the invention is not limited to these, but may be embodied in other ways within the subject matter defined in the following claims.

The invention claimed is:

1. An injection device for injecting a pharmaceutical liquid drug containing a preservative, comprising:
   a housing supporting a cartridge permanently embedded in the injection device, the cartridge having an interior chamber containing the pharmaceutical preservative containing liquid drug to be injected,
   a needle cannula permanently secured to the injection device, and usable for multiple injections and having a front part with a tip and a back part, which back part is adapted to be in liquid communication with the interior chamber of the cartridge, and
   a telescopic needle covering shield, which distally is provided with a reservoir confining a predetermined volume of a liquid for cleaning at least the tip of the needle cannula between subsequent injections, and which telescopic needle covering shield is urged distally into a first position by a first resilient member and moved proximally against the bias of the first resilient member into a second position during injection;
   the first position being a position in which, the tip of the front part of the needle cannula is located inside the reservoir, and
   the second position being a position in which, the tip of the front part of the needle cannula is located outside the reservoir and distally to the reservoir,
and wherein, the predetermined volume of liquid confined in the reservoir of the telescopic needle covering shield is the identical same pharmaceutical preservative containing liquid drug as present in the interior chamber of the cartridge, such that the identical same pharmaceutical preservative containing liquid drug is present in both the reservoir of the telescopic needle covering shield and in the interior chamber of the cartridge, and wherein the injection device automatically ejects a predetermined amount of pharmaceutical preservative containing liquid drug into the reservoir upon first use of the injection device.

2. The injection device according to claim 1, wherein the pharmaceutical preservative containing liquid drug is a blood sugar regulating drug comprising insulin, insulin analog, GLP-1 or GLP-2.

3. The injection device according to claim 1, wherein the needle cannula is secured in a hub.

4. The injection device according to claim 1, wherein the reservoir of the telescopic shield distally is provided with a distal septum and proximally with a proximal septum.

5. The injection device according to claim 4, wherein the proximal septum of the reservoir is movable relatively to the telescopic shield.

6. The injection device according to claim 4, wherein one or both of the distal septum and the proximal septum is provided with a carved-out portion surrounding the tip of the front part of the needle cannula in at least the first position.

7. A method of preparing an injection device for use, the method comprising the steps of:
   providing the injection device comprising:
      a housing supporting a cartridge permanently embedded in the injection device, the cartridge having an interior chamber containing the pharmaceutical preservative containing liquid drug to be injected,
      a needle cannula permanently secured to the injection device, and usable for multiple injections and having a front part with a tip and a back part, which back part is adapted to be in liquid communication with the interior chamber of the cartridge, and
      a telescopic needle covering shield, which distally is provided with a reservoir confining a predetermined volume of a liquid for cleaning at least the tip of the needle cannula between subsequent injections, and which telescopic needle covering shield is urged distally into a first position by a first resilient member and moved proximally against the bias of the first resilient member into a second position during injection;
         the first position being a position in which, the tip of the front part of the needle cannula is located inside the reservoir, and
         the second position being a position in which, the tip of the front part of the needle cannula is located outside the reservoir and distally to the reservoir,
      and wherein, the predetermined volume of liquid confined in the reservoir of the telescopic needle covering shield is the identical same pharmaceutical preservative containing liquid drug as present in the interior chamber of the cartridge, such that the identical same pharmaceutical preservative containing liquid drug is present in both the reservoir of the telescopic needle covering shield and in the interior chamber of the cartridge,
   holding the injection device with the telescopic needle shield in the first position such that the tip of the front part of the needle cannula is located inside the reservoir of the telescopic shield, and
   automatically ejecting a predetermined volume of the pharmaceutical preservative containing liquid drug contained inside the chamber of the cartridge into the reservoir of the telescopic shield upon first use of the injection device.

* * * * *

UNITED STATES PATENT AND TRADEMARK OFFICE
CERTIFICATE OF CORRECTION

PATENT NO. : 10,335,535 B2  
APPLICATION NO. : 15/032482  
DATED : July 2, 2019  
INVENTOR(S) : Bengtsson et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 223 days.

Signed and Sealed this  
Twenty-sixth Day of May, 2020

Andrei Iancu  
*Director of the United States Patent and Trademark Office*